(12) United States Patent
Macht et al.

(10) Patent No.: US 8,399,711 B2
(45) Date of Patent: Mar. 19, 2013

(54) PROCESS FOR PREPARING (METH)ACROLEIN BY HETEROGENEOUSLY CATALYZED GAS PHASE PARTIAL OXIDATION

(75) Inventors: Josef Macht, Mannheim (DE); Andreas Raichle, Dresden (DE); Klaus Joachim Mueller-Engel, Stutensee (DE); Ulrich Hammon, Mannheim (DE)

(73) Assignee: BASF SE, Ludwigshafen (DE)

( * ) Notice: Subject to any disclaimer, the term of this patent is extended or adjusted under 35 U.S.C. 154(b) by 153 days.

(21) Appl. No.: 12/954,770

(22) Filed: Nov. 26, 2010

(65) Prior Publication Data

US 2011/0130596 A1 Jun. 2, 2011

Related U.S. Application Data

(60) Provisional application No. 61/265,137, filed on Nov. 30, 2009.

(30) Foreign Application Priority Data

Nov. 30, 2009 (DE) .......................... 10 2009 047 291

(51) Int. Cl.
C07C 45/35 (2006.01)

(52) U.S. Cl. ........................................ 568/476; 568/479

(58) Field of Classification Search .................. 568/476, 568/479
See application file for complete search history.

(56) References Cited

U.S. PATENT DOCUMENTS

| 3,147,084 | A | 9/1964 | Franzen et al. | |
|---|---|---|---|---|
| 7,015,354 | B2 * | 3/2006 | Petzoldt et al. | ............... 562/547 |
| 7,608,734 | B2 | 10/2009 | Ha et al. | |

FOREIGN PATENT DOCUMENTS

| DE | 2 201 528 | | 1/1972 |
|---|---|---|---|
| DE | 25 13 405 | A1 | 10/1976 |
| DE | 28 30 765 | A1 | 1/1980 |
| DE | 29 03 218 | A1 | 8/1980 |
| DE | 29 09 671 | A1 | 10/1980 |
| DE | 40 23 239 | A1 | 1/1992 |
| DE | 197 17 165 | A1 | 10/1998 |
| DE | 198 55 913 | A1 | 6/2000 |
| DE | 199 55 176 | A1 | 1/2001 |
| DE | 199 48 248 | A1 | 4/2001 |
| DE | 199 48 523 | A1 | 4/2001 |
| DE | 199 55 168 | A1 | 5/2001 |
| DE | 100 46 957 | A1 | 4/2002 |
| DE | 101 01 695 | A1 | 7/2002 |
| DE | 103 13 209 | A1 | 3/2004 |
| DE | 103 37 788 | A1 | 10/2004 |
| DE | 103 61 515 | A1 | 7/2005 |
| DE | 10 2004 017 150 | A1 | 10/2005 |
| DE | 10 2006 015 710 | A1 | 4/2007 |
| DE | 10 2006 000 996 | A1 | 7/2007 |
| DE | 10 2007 004 961 | A1 | 7/2008 |
| DE | 10 2008 040 093 | A1 | 12/2008 |
| DE | 10 2008 040 094 | A1 | 1/2009 |
| DE | 10 2008 042 060 | A1 | 6/2009 |
| DE | 10 2008 042 061 | A1 | 3/2010 |
| DE | 10 2008 042 064 | A1 | 3/2010 |
| DE | 10 2008 054 586 | A1 | 6/2010 |
| EP | 0 279 374 | A1 | 8/1988 |
| EP | 0 293 859 | A1 | 12/1988 |
| EP | 0 383 224 | A2 | 8/1990 |
| EP | 0 575 897 | A1 | 12/1993 |
| EP | 0 700 714 | A1 | 3/1996 |
| EP | 0 714 700 | A2 | 6/1996 |
| EP | 1 180 508 | A1 | 2/2002 |
| EP | 1 270 065 | A1 | 1/2003 |
| EP | 1 449 579 | A1 | 8/2004 |
| WO | WO 2004/009525 | A1 | 1/2004 |
| WO | WO 2004/085369 | A1 | 10/2004 |
| WO | WO 2005/005037 | A1 | 1/2005 |
| WO | WO 2005/030393 | A1 | 4/2005 |
| WO | WO 2005/042459 | A1 | 5/2005 |
| WO | WO 2005/047224 | A1 | 5/2005 |
| WO | WO 2007/082827 | A1 | 7/2007 |
| WO | WO 2008/087115 | A2 | 7/2008 |
| WO | WO 2009/125658 | A1 | 10/2009 |

OTHER PUBLICATIONS

U.S. Appl. No. 13/362,607, filed Jan. 31, 2012, Allardt, et al.
"Ullmann's Encyclopedia of Industrial Chemistry", Fifth, Completely Revised Edition, vol. B4, "Principles of Chemical Reaction Engineering and Plant Design", (Editors: Barbara Elvers, et al.), 1992, pp. 21-22.

* cited by examiner

Primary Examiner — Sikarl Witherspoon
(74) Attorney, Agent, or Firm — Oblon, Spivak, McClelland, Maier & Neustadt, L.L.P.

(57) ABSTRACT

A process for preparing (meth)acrolein by heterogeneously catalyzed gas phase partial oxidation of a precursor compound, in which the reaction gas mixture which comprises at least 3% by volume of precursor compound is passed through a fresh fixed catalyst bed whose active material is a multielement oxide which comprises the elements Mo, Fe and Bi and at least one of the elements Ni and Co, and the fixed catalyst bed is loaded with at least 40 l (STP)/l·h of precursor compound, and the precursor compound is converted to an extent of at least 90 mol %, wherein, over the first 8000 operating hours, during X=10 to 500 operating hours, the highest temperature of the reaction gas mixture in the fixed catalyst bed is 400 to 450° C. and, during the remaining 8000–X operating hours, is 300 to <400° C., and the loading of the fixed catalyst bed with organic precursor compound, averaged over the time, for the X=10 to 500 operating hours is greater than for the 8000–X operating hours.

10 Claims, No Drawings

PROCESS FOR PREPARING (METH)ACROLEIN BY HETEROGENEOUSLY CATALYZED GAS PHASE PARTIAL OXIDATION

The present invention relates to a process for preparing (meth)acrolein by heterogeneously catalyzed gas phase partial oxidation, in which a reaction gas mixture is passed at elevated temperature through a fresh fixed catalyst bed present in a reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst bed is at least one multielement oxide which comprises the elements Mo, Fe and Bi and additionally at least one of the two elements Ni and Co.

In this document, "(meth)acrolein" is abbreviated notation for "methacrolein or acrolein".

Acrolein and methacrolein are reactive monomers which are of significance especially as intermediates for preparing acrylic acid or methacrylic acid.

On the industrial scale, (meth)acrolein is prepared predominantly by heterogeneously catalyzed gas phase partial oxidation of $C_3$ or $C_4$ precursor compounds as organic precursor compounds. For the preparation of acrolein, for example, the $C_3$ precursor compounds propane, propylene, glycerol and n-propanol can be used. For the preparation of methacrolein, the $C_4$ precursor compounds used may, for example, be isobutane, isobutene or isobutanol, the latter being obtainable in situ from the methyl ether thereof.

One group of catalysts to be used with preference for these gas phase partial oxidations is that of catalysts which are in the solid state and whose active materials are multielement oxides which comprise at least the elements Mo, Fe and Bi, and additionally at least one of the two elements Co and Ni (cf., for example, EP-A 1 449 579, EP-A 279 374, DE-A 10 2006 015710, DE-A 103 37 788, WO 2009/125658, WO 2007/082827, WO 2005/042459, WO 2004/085369, WO 2005/030393 and WO 2008/087115).

Typically, the heterogeneously catalyzed gas phase partial oxidation of the at least one organic precursor compound to (meth)acrolein is performed by passing a reaction gas mixture which, as well as the at least one organic precursor compound to be partially oxidized, comprises molecular oxygen as an oxidizing agent at elevated temperature through a fixed catalyst bed comprising the catalysts. The exothermic chemical conversion proceeds during the residence time of the reaction gas mixture over the catalyst surface. Based on a single pass of the reaction gas mixture through the fixed catalyst bed, the resulting conversion of the organic precursor compound is generally $\geq 90$ mol %.

The fixed catalyst bed is normally surrounded by a shell (for example, it may be present in the catalyst tubes of a tube bundle reactor or in the spaces between the plates of a thermoplate reactor). On the inside of the shell, the exothermic partial oxidation proceeds during the residence time over the catalyst surface, and beyond the shell a heat carrier (for example a salt bath) is conducted in order to absorb and to remove the heat of reaction.

In addition, the reactants are generally diluted with a gas which is essentially inert under the conditions of the gas phase partial oxidation, which, with its heat capacity, is additionally capable of absorbing heat of reaction released and in most cases simultaneously has a favorable influence on the explosion behavior of the reaction gas mixture.

Typically, the inert diluent gases used may be either combustible or noncombustible gases. One of the most frequently used inert diluent gases is molecular nitrogen, which is always automatically employed when the oxygen source used for the heterogeneously catalyzed gas phase partial oxidation is air. Another frequently used diluent gas is, owing to its general availability, steam. In many cases, cycle gas is also used as an inert diluent gas (cf., for example, EP-A 1180508). Cycle gas refers to the residual gas which remains in the heterogeneously catalyzed gas phase partial oxidation of the at least one organic precursor compound when the target product (generally acrylic acid or methacrylic acid since the (meth)acrolein is generally merely an intermediate which is oxidized further in a subsequent partial oxidation stage to acrylic acid or methacrylic acid) has been removed more or less selectively (for example by absorption into a suitable solvent or by fractional condensation) from the product gas mixture resulting from the partial oxidation. In general, it consists predominantly of the inert diluent gases used for the heterogeneously catalyzed gas phase partial oxidation, and of steam formed as a by-product in the gas phase partial oxidation, and carbon oxides formed by undesired full secondary oxidation. In some cases, it comprises small amounts of molecular oxygen unconsumed in the gas phase partial oxidation (residual oxygen) and/or of unconverted organic starting compounds. Typically, only a portion of the residual gas is used as cycle gas. The remaining amount of residual gas is typically combusted.

In general, acrylic acid or methacrylic acid (in this document, the notation "(meth)acrylic acid" is also used as an abbreviation for "acrylic acid or methacrylic acid") is additionally formed in relatively small amounts in the preparation of (meth)acrolein performed as described. Not least because (meth)acrolein is frequently merely a desired intermediate in the course of an attempted preparation of (meth)acrylic acid, the term "target product" in this application always comprises the sum of (meth)acrolein and (meth)acrylic acid.

The further oxidation of the (meth)acrolein to (meth)acrylic acid in a downstream oxidation stage is normally effected over a separate fixed catalyst bed tailored for this reaction step (the active material of the corresponding catalysts is generally likewise a multielement oxide which comprises the elements Mo and V and normally Cu). Overall, reference is then made to a two-stage gas phase partial oxidation for preparation of (meth)acrylic acid. In the first stage, predominantly (meth)acrolein is formed, and the product gas mixture leaving the first stage is then, optionally after intermediate cooling and/or supplementation of molecular oxygen and optionally inert gas (both together, for example, in the form of air), conducted directly into the second stage, where the (meth)acrolein formed in the first stage is oxidized further to (meth)acrylic acid. The temperature level of the first stage is typically above the temperature level of the second stage. Both stages can be performed in spatially separate reactors, connected in series, or else in one reactor ("single reactor") over fixed catalyst beds arranged in succession therein.

"Ullmanns Encyclopedia of Industrial Chemistry, Fifth, Completely Revised Edition, Volume B4, 1992, VCH Verlag D-6940 Weinheim, p. 21" discloses that, irrespective of how heat carrier and reaction gas mixture are conducted relative to one another in the fixed bed reactor and are configured individually, the temperature of the reaction gas mixture in the course of reactive passage through the fixed catalyst bed normally does not have an isothermal temperature profile. Instead, the temperature of the reaction gas mixture in the course of reactive flow through the fixed catalyst bed normally passes through a "maximum temperature", which is also referred to in the technical literature as the hotspot.

This is not least because the heat of reaction, on the one hand, has to be removed with a sufficient rate to avoid overheating of the system. On the other hand, the heat removal must not be too rapid, since the reaction may otherwise stop. Conversely, the reaction, especially on commencement thereof, must evolve heat to a sufficient degree to start at all. This balance is complicated by the fact that the reactant concentration in the course of flow through the fixed catalyst bed is not constant, but decreases proceeding from its starting value. In the outlet region of the reaction gas mixture from the fixed catalyst bed, this reduces the reaction rate and the associated evolution of heat, while the high reactant concentration in the inlet region of the reaction gas mixture into the catalyst charge accelerates the exothermic evolution of heat.

Following the recommendations of the prior art, processes for heterogeneously catalyzed gas phase partial oxidation for preparation of (meth)acrolein over multielement oxide active materials comprising the elements Mo, Fe and Bi and additionally at least one of the two elements Ni and Co should generally be performed in such a way that the maximum temperature of the reaction gas mixture as it flows through the fixed catalyst bed is at a minimum (cf., for example, U.S. Pat. No. 7,608,734, WO 2004/085369, WO 2005/042459 and WO 2007/082827). Especially temperatures of $\geq 400°$ C. should be avoided as far as possible.

A characteristic which is gaining increasing significance for heterogeneously catalyzed partial gas phase oxidation for preparation of (meth)acrolein is the selectivity of target product formation ($S^z$).

This is understood to mean the ratio of the molar total amount of target product (in this application (meth)acrolein+(meth)acrylic acid) formed in the course of passage of the reaction gas mixture through the fixed catalyst bed to the molar total amount of organic precursor compound converted in the course of passage of the reaction gas mixture through the fixed catalyst bed. This ratio is typically multiplied by 100 mol % and $S^z$ is reported in mol %.

$S^z$ is a measure of how much desired target product can be obtained from a given amount of organic precursor compound in the course of performance of the heterogeneously catalyzed partial gas phase oxidation. Especially in times of increasingly scarce resources and rising raw material costs, interest in maximum values of $S^z$ has grown.

Detailed studies by the inventors of the present patent application have led to the result that, in the processes for heterogeneously catalyzed partial gas phase oxidation relevant for the invention, in the case of a startup of a fresh fixed catalyst bed following the recommendations of the prior art, $S^z$ initially increases comparatively slowly during the first 8000 operating hours of the fresh fixed catalyst bed, finally attains a steady-state value and subsequently essentially maintains this value in the course of further process execution over comparatively long operating times, before the selectivity of target product formation finally decreases again owing to increasing catalyst deactivation with retention of the reactant conversion.

In view of this prior art, it was an object of the present invention, in the context of a preparation of (meth)acrolein by heterogeneously catalyzed gas phase partial oxidation of an organic compound to be partially oxidized, to provide a process for startup of a fresh fixed catalyst bed which ensures an improved selectivization of the fresh fixed catalyst bed.

Accordingly, a process for preparing (meth)acrolein by heterogeneously catalyzed gas phase partial oxidation, in which a reaction gas mixture is passed at elevated temperature through a fresh fixed catalyst bed present in a reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst bed is at least one multielement oxide which comprises the elements Mo, Fe and Bi and additionally at least one of the two elements Ni and Co is provided, wherein the process, over the first 8000 operating hours of the fresh fixed catalyst bed, during which the reaction gas mixture supplied to the fixed catalyst bed at a loading of the fixed catalyst bed with the organic precursor compound of at least 40 l (STP)/l·h comprises at least 3% by volume of the organic precursor compound to be partially oxidized and, based on a single pass of the reaction gas mixture through the fixed catalyst bed, at least 90 mol % of the organic precursor compound present therein is converted and the highest temperature $T^H$ of the reaction gas mixture in the course of passage through the fixed catalyst bed is at least 300° C., is performed such that, during X=10 to 500 operating hours, the highest temperature $T^H$ of the reaction gas mixture as it passes through the fixed catalyst bed is 400 to 450° C. and, during the remaining 8000–X operating hours, is less than 400° C., and the loading of the fixed catalyst bed with the at least one organic precursor compound to be partially oxidized, averaged arithmetically over the time, for the X=10 to 500 operating hours is greater than for the 8000–X operating hours.

A fresh fixed catalyst bed shall be understood in this document to mean a fixed catalyst bed with which the reactor has been freshly charged. A fresh charge is always present when the reactor has never before been charged with catalyst for the same reaction and is (has been) thus charged for the first time with a fixed catalyst bed suitable therefor, or when the process for preparing (meth)acrolein by heterogeneously catalyzed gas phase partial oxidation has already been performed beforehand over a fixed catalyst bed in the same reactor and at least a portion of the catalysts of this fixed catalyst bed is or has been replaced by fresh catalysts (cf., for example, WO 2005005037 and WO 2004009525). This is especially true when at least 5% by weight, or at least 10% by weight, or at least 20% by weight, or at least 30% by weight, or at least 40% by weight, or at least 60% by weight, or at least 80% by weight, of the catalysts of the fixed catalyst bed already utilized as described above is replaced by fresh catalysts. Of course, the above is also true especially when the total amount of the catalysts of this fixed catalyst bed is replaced (or has been replaced) by fresh catalysts.

The inventive procedure is found to be favorable especially when X is 20 to 450, advantageously 30 to 400, preferably 40 to 350, more preferably 50 to 300 and favorably 75 to 275 operating hours.

It is also advantageous when $T^H$ within the X operating hours does not assume excessively high values. In other words, favorable values for $T^H$ during the X operating hours are 405 to 445° C., or 405 to 440° C., preferably 410 to 435° C., or 410 to 430° C. Appropriately in application terms, $T^H$ during the X operating hours is 400 to 430° C., or 405 to 425° C. or 400 to 420° C.

During the remaining 8000–X operating hours, $T^H$, following the teaching of the prior art and advantageously, will be 300 to 399° C., or to 398° C., or to 395° C., or 310 to 390° C., or 320 to 385° C., or 330 to 380° C., or 340 to 370° C.

Appropriately in application terms, $T^H$ during the remaining 8000−X operating hours is 340 to 395° C. or 345 (or 350) to 390° C.

Operating hours during which $T^H$ is below 300° C. shall be considered as nonoperating hours in the context of the present invention, since there is essentially no stress on the fixed catalyst bed which is relevant for the invention under such operating conditions (the reaction temperatures in this case are too low for appropriate conversions of the organic precursor compounds to be partially oxidized).

It will be appreciated that the process according to the invention may temporarily also be interrupted for other reasons (also comprise other nonoperating hours). Such a nonoperating stage exists, for example, when the fixed catalyst bed, following the recommendations of WO 2005/042459 or WO 2005/047224, is intermediately regenerated.

Nonoperating hours shall also exist when the gas mixture (reaction gas mixture) supplied to the fixed catalyst bed loads the fixed catalyst bed at less than 40 l (STP)/l·h of the organic precursor compound, comprises less than 3% by volume of the organic precursor compound to be partially oxidized and/or, based on a single pass of the reaction gas mixture through the fixed catalyst bed, less than 90 mol % of the organic precursor compound present therein is converted. Such nonoperating hours should not be taken into account (are not included) in the 8000 operating hours which are relevant for the invention. In other words, catalysts which have passed only through nonoperating states in the aforementioned sense are still included under "fresh catalysts" in the sense of the present application, and a fixed catalyst bed charged with them is still a "fresh fixed catalyst bed".

The loading of the fixed catalyst bed with the reaction gas mixture supplied to the fixed catalyst bed is understood in this document to mean the amount of reaction gas mixture in standard liters (=l (STP); the volume in liters that the corresponding amount of reaction gas mixture would occupy under standard conditions (i.e. at 0° C. and 1 atm=101325 Pa)) which is conducted through one liter of fixed catalyst bed per hour (upstream and downstream beds of pure inert material are not counted as part of the fixed catalyst bed; homogeneous mixtures of shaped inert material bodies and shaped catalyst bodies are, in contrast, counted as part of the fixed catalyst bed (and of the bed volume thereof)).

The loading may also be based only on one constituent of the reaction gas mixture. In that case, it is the volume of this constituent which is supplied to the fixed catalyst bed, based on the volume of the bed thereof, per hour.

It is essential to the process according to the invention that the loading of the fixed catalyst bed with the at least one organic precursor compound to be partially oxidized, averaged arithmetically over the time, for the X operating hours is greater than for the 8000−X operating hours.

When, in the process according to the invention, the loading of the fixed catalyst bed with the at least one organic precursor compound to be partially oxidized is plotted as the ordinate against the X operating hours (or against the 8000−X operating hours) as the abscissa, the area present under the resulting curve in the time range from t=0 h to the time t=X h (or t=(8000−X) h) divided by X h (or by (8000−X) h) constitutes the abovementioned loading of the fixed catalyst bed arithmetically averaged over the particular operating time.

It is possible to influence $T^H$ in different ways in the process according to the invention. Direct influence can be effected by varying the temperature of the heat carrier conducted around the shell of the fixed catalyst bed to absorb the heat of reaction. When this temperature is increased (lowered) under otherwise unchanged reaction conditions, this is normally also directly associated with an increase (lowering) of $T^H$. $T^H$ can, however, also be altered under otherwise unchanged reaction conditions, for example, by varying the loading of the fixed catalyst bed with the at least one organic precursor compound to be partially oxidized.

When this loading of the fixed catalyst bed with the at least one organic precursor compound to be partially oxidized is increased (lowered) under otherwise unchanged reaction conditions and with a constant feed stream of reaction gas mixture into the fixed catalyst bed, this is normally also directly associated with an increase (lowering) of $T^H$.

The aforementioned is especially true when the increase in the loading of the fixed catalyst bed with the at least one organic precursor compound to be partially oxidized is implemented in such a way that not only the proportion of the organic precursor compound (in % by volume) in the reaction gas mixture which is supplied to the fixed catalyst bed, but appropriately additionally also the proportion by volume of the molecular oxygen in the reaction gas mixture, is increased, such that the molar ratio of the two reactants in the reaction gas mixture remains essentially unchanged.

$T^H$ typically also increases significantly when, with homogeneous composition of the reaction gas mixture, in addition to an increase in the temperature of the heat carrier, the loading of the fixed catalyst bed with reaction gas mixture is increased (associated with this, an increase in the loading of the fixed catalyst bed with the at least one organic precursor compound to be partially oxidized is simultaneously brought about).

Of course, under otherwise unchanged reaction conditions, an increase in $T^H$ can also be brought about by increasing both the loading of the fixed catalyst bed with reaction gas mixture and the proportion by volume of the at least one organic precursor compound to be partially oxidized in the reaction gas mixture. It is also possible for above loading variations to be accompanied additionally by variations in the temperature of the heat carrier.

Further influences on $T^H$ can be undertaken by varying the proportion by volume and/or the type of inert diluent gas in the reaction gas mixture. An increase in the partial pressure of the at least one organic precursor compound to be partially oxidized in the reaction gas mixture supplied to the fixed catalyst bed leads, under otherwise unchanged reaction conditions (more particularly also with a stable composition of the reaction gas mixture supplied to the fixed catalyst bed) likewise to an increase in $T^H$. Frequently, such a partial pressure increase is accompanied by an increase in the working pressure.

Diluent gases which are essentially inert under the conditions of the heterogeneously catalyzed gas phase partial oxidation are understood to mean those diluent gases whose constituents, under the conditions of the heterogeneously catalyzed gas phase partial oxidation—each constituent considered alone—are preserved unchanged to an extent of more than 95 mol %, preferably to an extent of more than 99 mol % (in simplified terms, such gases are in many cases also referred to as inert diluent gases). When an inert diluent gas with a comparatively low molar heat capacity Cp (for example molecular nitrogen) is replaced under otherwise unchanged reaction conditions by an inert diluent gas with a comparatively elevated molar heat capacity Cp (for example n-propane), $T^H$ generally falls.

It will be appreciated that the molar $O_2$:organic precursor compound ratio selected for the reaction gas mixture, under otherwise unchanged reaction conditions, also influences the $T^H$ which is established.

Advantageously in accordance with the invention, during at least 20%, preferably during at least 40%, more preferably during at least 60%, even more preferably during at least 80% and at best during the entire duration, of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000–X operating hours.

The most favorable case in accordance with the invention is when, over the entire X operating hours, the loading of the fixed catalyst bed with the at least one organic precursor compound to be partially oxidized is greater than the greatest loading of the fixed catalyst bed with the at least one organic precursor compound to be partially oxidized employed during the 8000–X operating hours.

Appropriately in application terms, the loading of the fixed catalyst bed with the at least one organic precursor compound to be partially oxidized, averaged arithmetically over the time, for the X operating hours is at least 5%, or at least 10%, or at least 20%, or at least 30%, preferably at least 40%, or at least 50%, better at least 60%, or at least 70%, or at least 80%, and even better at least 90%, or at least 100%, or at least 120%, or at least 150%, greater than for the 8000–X operating hours (the latter forming the reference basis for the calculation of the percentage difference).

In general, the loading of the fixed catalyst bed with the at least one organic precursor compound to be partially oxidized, averaged arithmetically over the time, for the X operating hours will, however, be $\leq$300%, frequently $\leq$200% (in the case of performance of the process in reactors with only one temperature zone also $\leq$100%), above that for the 8000–X operating hours (the latter again forming the reference basis for the calculation of the percentage difference).

Advantageously in accordance with the invention, the loadings of the fixed catalyst bed with the at least one organic precursor compound to be partially oxidized, employed during the X operating hours, will differ by not more than ±50 l (STP)/l·h, better by not more than ±40 l (STP)/l·h, even better by not more than ±30 l (STP)/l·h and particularly advantageously by not more than ±20 l (STP)/l·h or by not more than ±10 l (STP)/l·h, from the arithmetic mean thereof formed over the X operating hours.

Advantageously in accordance with the invention in the same way, the loadings of the fixed catalyst bed with the at least one organic precursor compound to be partially oxidized, employed during the 8000–X operating hours, will differ by not more than ±50 l (STP)/l·h, better by not more than ±40 l (STP)/l·h, even better by not more than ±30 l (STP)/l·h and particularly advantageously by not more than ±20 l (STP)/l·h or by not more than ±10 l (STP)/l·h, from the arithmetic mean thereof formed over the 8000–X operating hours.

The reason for the advantage of the inventive procedure, of accompanying the relatively high temperatures $T^H$ in the operating period of the X operating hours essentially simultaneously by higher loadings of the fixed catalyst bed with the at least one organic precursor compound to be partially oxidized, is that such elevated loadings have a damping effect on the conversion (based on a single pass of the reaction gas mixture through the fixed catalyst bed) which results under the otherwise given conditions of the at least one organic precursor compound to be partially oxidized. An increasing conversion of the at least one organic precursor compound to be partially oxidized, however, generally reduces the selectivity of formation of the organic target compound.

In other words, if the raising of $T^H$ during the X operating hours compared to the 8000–X operating hours were to be brought about exclusively by an increase in the temperature of the heat carrier, $S^z$ would be reduced comparatively during the X operating hours.

Surprisingly, the operation of the fixed catalyst bed at an elevated temperature $T^H$ during the X operating hours brings about an accelerated selectivization of the fixed catalyst bed, without significantly impairing it.

The earlier the position of the X operating hours (within the 8000 operating hours), the greater the advantage of the inventive procedure.

Advantageously in accordance with the invention, the total number of the X operating hours in the process according to the invention is therefore within the first 7000, preferably within the first 6000, of the first 8000 operating hours relevant for the invention.

More preferably in accordance with the invention, the entirety of the X operating hours in the process according to the invention is therefore within the first 5000, better within the first 4000 and even better within the first 3000 of the first 8000 operating hours which are relevant for the invention.

Most preferably in accordance with the invention, the entirety of the X operating hours in the process according to the invention is therefore within the first 2500, better within the first 2000, even better within the first 1500, particularly advantageously within the first 1000, or within the first 800, or within the first 600, of the 8000 operating hours relevant for the invention.

In principle, the X operating hours in the process according to the invention can constitute the start of the first 8000 operating hours relevant for the invention. Appropriately in application terms, the procedure in the first 20 to first 250 of the first 8000 operating hours relevant for the invention will, however, be according to the recommendations of the prior art, and $T^H$ will be kept below 400° C. during these operating hours. Particularly advantageously, the procedure within these first 20 to first 250 operating hours will be as described in DE-A 103 37 788. Advantageously in accordance with the invention, the X operating hours will then be followed by the $T^H$ increased in accordance with the invention.

Preferably in accordance with the invention, the inventive X operating hours will not be distributed in an irregular manner over the first 8000 operating hours. Instead, advantageously in application terms, the inventive X operating hours (apart from production shutdowns or nonoperating states required for other reasons) will be implemented (positioned) "en bloc".

It will be appreciated that, employing the inventive procedure, the inventive X operating hours can also be employed in a homogeneously or inhomogeneously blurred manner over the first 8000 operating hours. When X overall exceeds 500 operating hours, the associated impairment in the other properties of the fixed catalyst bed becomes increasingly less negligible. When X overall is below 10 operating hours, the resulting advantage is barely apparent.

When the fixed catalyst bed in the process according to the invention is present in a reactor which has more than one temperature zone (for example two temperature zones), with the proviso that each of the temperature zones is charged spatially separately with a separate (independent) heat carrier, as recommended, for example, by U.S. Pat. No. 7,608,734, WO 2007/082827, WO 2004/085369 and the prior art acknowledged in these documents, the temperature of the reaction gas mixture in the course of reactive flow through the fixed catalyst bed within each of the temperature zones may pass through a maximum temperature (a relative temperature maximum based on the particular temperature zone). The "temperature $T^H$" of the reaction gas mixture used in this document means, in these cases, the highest of the aforementioned relative temperature maxima which are generally different from one another. Typically, this maximum is present within the first temperature zone in flow direction of the reaction gas mixture.

However, owing to the spatially separate conduction of heat carrier in the different temperature zones, the procedure may also be such that the characterizing part of the inventive procedure is applied to each of the relative temperature maxima of the reaction gas mixture present in the different temperature zones.

Appropriately in application terms, in the inventive procedure, the reaction gas mixture will be supplied preheated to that temperature that the heat carrier has where the reaction gas mixture enters the fixed catalyst bed.

Otherwise, the process according to the invention, outside the inventive X operating hours, both within the first 8000 operating hours and after the first 8000 operating hours, will be operated following the recommendations of WO 2005/042459 or WO 2007/082827 for the corresponding partial oxidation stage.

The conversion of the at least one organic precursor compound to be partially oxidized (based on single pass of the reaction gas mixture through the fixed catalyst bed) is, in the process according to the invention, within the first 8000 operating hours, appropriately in application terms set essentially homogeneously to the desired target conversion, which is $\geq 90$ mol %. "Essentially homogeneously" means that the maximum deviation from the conversion averaged arithmetically over the time (the first 8000 operating hours) deviates by not more than ±5 mol %, or not more than ±3 mol % (the reference basis is the conversion averaged arithmetically over the time (the first 8000 operating hours)).

Appropriately in application terms, the process according to the invention is performed at conversions C of the at least one organic precursor compound to be partially oxidized (based on a single pass of the reaction gas mixture through the fixed catalyst bed) of $\geq 92$ mol %, preferably $\geq 94$ mol %, or $\geq 96$ mol %. In general, C in the process according to the invention is, however, $\leq 99$ mol %.

The conversion C is understood to mean the ratio of the difference between the molar flow of the at least one organic precursor compound supplied to the fixed catalyst bed (as a constituent of the reaction gas input mixture supplied to the fixed catalyst bed) and that removed (as a constituent of the product gas mixture removed from the fixed catalyst bed) relative to the molar flow of the at least one organic precursor compound supplied to the fixed catalyst bed (in general, this ratio is multiplied by 100 mol % and C is reported in mol %).

It has been found to be advantageous for the inventive procedure when, especially during the X operating hours, the product gas mixture still comprises at least 0.1% by volume, preferably at least 0.2% by volume and more preferably at least 0.3% by volume or at least 0.5% by volume of the at least one precursor compound to be partially oxidized (for example of the propylene). Normally, the aforementioned residual content will, however, be $\leq 1\%$ by volume.

The loading of the fixed catalyst bed with the at least one organic precursor compound to be partially oxidized (preferably propylene) in the process according to the invention (especially during the first 8000 operating hours) will normally be $\geq 50$ to $\leq 300$ l (STP)/l·h, advantageously $\geq 75$ to $\leq 250$ l (STP)/l·h, preferably $\geq 90$ to $\leq 200$ l (STP)/l·h and particularly frequently $\geq 100$ to $\leq 150$ l (STP)/l·h. Especially in the case of loading values of $\geq 130$ l (STP)/l·h, an implementation of the inventive procedure in a multizone reactor (especially in a two-zone reactor) becomes increasingly advantageous (cf. WO 2007/082827).

The inert gas present in the reaction gas mixture may, in the process according to the invention, consist of molecular nitrogen to an extent of $\geq 20\%$ by volume, or to an extent of $\geq 30\%$ by volume, or to an extent of $\geq 40\%$ by volume, or to an extent of $\geq 50\%$ by volume, or to an extent of $\geq 60\%$ by volume, or to an extent of $\geq 70\%$ by volume, or to an extent of $\geq 80\%$ by volume, or to an extent of $\geq 90\%$ by volume, or to an extent of $\geq 95\%$ by volume.

Especially in the case of loadings of the fixed catalyst bed with the at least one organic precursor compound to be partially oxidized of $\geq 150$ l (STP)/l·h or $\geq 200$ l (STP)/l·h, an increasing additional use of inert diluent gases with an increased molar specific heat Cp, as possessed, for example, by propane, $CO_2$, methane and steam, is advisable for the process according to the invention.

The working pressure in the process according to the invention (especially in the case of a propylene partial oxidation) may be either below standard pressure (for example up to 0.5 bar) or above standard pressure. Typically, the working pressure will be at values of 1 to 5 bar, frequently 1.5 to 3.5 bar. Normally, the reaction pressure will not exceed 100 bar (all working pressures should be understood as absolute pressures).

The molar ratio V of $O_2$:organic precursor compound in the reaction gas mixture supplied to the fixed catalyst bed is, in accordance with the invention, $\geq 1$. Typically, this ratio will be at values of $\leq 3$. Frequently, this ratio will be $\geq 1.5$ and $\leq 2.0$.

Advantageously in accordance with the invention, V, especially during the X operating hours, will be $\geq 1$ and $\leq 1.5$, or $\geq 1.1$ and $\leq 1.40$ or $\geq 1.20$ and $\leq 1.40$ (in a downstream acrolein partial oxidation stage, preceding intermediate feeding of air to the product gas mixture of the first oxidation stage can advantageously counteract a propagation of such reduced V values from the first oxidation stage into the second oxidation stage). During the 8000–X operating hours, it is, in contrast, favorable when V is $>1.5$ and $\leq 3$.

Useful sources for the molecular oxygen required in the reaction gas mixture for the process according to the invention are both air (preferably) and, for example, molecular nitrogen-depleted air (for example $\geq 90\%$ by volume of $O_2$ and $\leq 10\%$ by volume of $N_2$).

All remarks made in this document are valid especially when the organic precursor compound to be partially oxidized is propylene.

The proportion A of the at least one organic precursor compound to be partially oxidized in the reaction gas mixture supplied to the fixed catalyst bed in the process according to the invention will generally (especially when propylene is the precursor compound) be $\geq 4\%$ by volume, usually $\geq 5\%$ by volume. Frequently, A (especially when propylene is the precursor compound) will be 4 to 15% by volume, preferably 5 to 12% by volume and advantageously 5 to 8% by volume (based in each case on the total volume).

Frequently, the process according to the invention will be performed at an organic precursor compound:molecular oxygen:inert gas (including steam) volume ratio in the reaction gas mixture supplied (also referred to as charge gas mixture or reaction gas input mixture) of 1:(1.0 to 3.0):(5 to 25), preferably 1:(1.5 to 2.3):(10 to 15). The above is especially true when propylene is the organic precursor compound. It will be appreciated that the charge gas mixtures used for the process according to the invention may, however, also be all of those recommended in the prior art documents acknowledged in this application (for example those recommended by DE-A 103 37 788 and DE-A 103 13 209 or WO 2007/082827).

When the process according to the invention forms the first reaction stage of a two-stage heterogeneously catalyzed partial oxidation for preparation of acrylic acid (e.g. propylene→acrolein→acrylic acid), an increase in the loading of the fixed catalyst bed with the at least one organic precursor compound to be partially oxidized in the first reaction stage in the X operating hours, as a result, is normally also accompanied by an increase in the loading of the fixed catalyst bed with acrolein in the second reaction stage (especially when the conversion in the first partial oxidation stage is maintained).

The active material of the catalysts of such a second gas phase partial oxidation stage is normally at least one multielement oxide comprising Mo and V (cf., for example, DE-A 103 37 788, WO 2005/042459, WO 2007/082827 and WO 2004/085369). They do not exhibit the inventive selectivization effect. The operation of the second partial oxidation stage (acrolein→acrylic acid) therefore, advantageously in application terms, strictly follows the recommendations of the prior art and always avoids elevated maximum temperatures of the reaction gas mixture flowing through the fixed catalyst bed of the second partial oxidation stage.

In general, the second partial oxidation stage will therefore be operated as described in documents DE-A 103 37 788, WO 2005/042459, WO 2007/082827 and WO 2004/085369 in such a way that the maximum temperature of the reaction gas mixture in the second partial oxidation stage is $\leq 350°$ C., preferably $\leq 340°$ C. and more preferably $\leq 330°$ C. In general, the maximum temperature of the reaction gas mixture in the second partial oxidation stage will, however, be $\geq 250°$ C., preferably $\geq 260°$ C. and more preferably $\geq 270°$ C. The conversion of the acrolein in the second partial oxidation stage is regularly kept at values of $\geq 99.5$ mol %, or $\geq 99.7$ mol %, or $\geq 99.8$ mol %.

For the process according to the invention, suitable compounds as the at least one organic precursor compound in the case of preparation of acrolein include propane, propylene, glycerol and n-propanol, among which propylene is particularly preferred. In the case of preparation of methacrolein, suitable compounds as the at least one organic precursor compound include isobutane, isobutene or isobutanol, or the methyl ether of isobutanol, among which isobutene is preferred.

The active material of the catalysts of the fixed catalyst bed in the process according to the invention is multielement oxides which comprise at least the elements Mo, Fe and Bi, and additionally at least one of the two elements Ni and Co. Among the aforementioned five elements, preferably in accordance with the invention, based on the molar total amount G thereof present in the active material, the element Mo accounts for the greatest molar proportion (in mol % based on the molar total amount G).

Multielement oxide active materials particularly suitable in accordance with the invention are thus especially those of the general formula I of DE-A 19955176, the multielement oxide active materials of the general formula I of DE-A 19948523, the multielement oxide active materials of the general formulae I, II and III of DE-A 10101695, the multielement oxide active materials of the general formulae I, II and III of DE-A 19948248 and the multielement oxide active materials of the general formulae I, II and III of DE-A 19955168, and also the multielement oxide active materials specified in documents EP-A 700 714, DE-A 10 2007 004961, DE-A 10 2008 040093, DE application 102008042064.6, DE application 102008042061.1 and DE-A 102008042060. This is especially true of the exemplary embodiments disclosed in the latter five documents. Equally suitable as multielement oxide active materials for the process according to the invention are those recommended in WO 2007/082827 and in WO 2005/042459 for the heterogeneously catalyzed partial gas phase oxidation.

A multitude of the multielement oxide active materials suitable for the process according to the invention can be encompassed by the general formula I

$$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.05 to 5,
b=0.01 to 5, preferably 2 to 4,
c=0.1 to 10, preferably 3 to 10,
d=0 to 2, preferably 0.02 to 2,
e=0 to 8, preferably 0 to 5,
f=0 to 10 and
n=a number which is determined by the valency and frequency of the elements in I other than oxygen.

They are obtainable in a manner known per se (see, for example, DE-A 40 23 239) and are typically used shaped in substance to spheres, rings or cylinders, or else in the form of eggshell catalysts, i.e. preshaped inert support bodies coated with the active material. It will be appreciated, however, that they may also be employed in powder form as catalysts.

In principle, active materials of the general formula I can be prepared in a simple manner by obtaining, from suitable sources of the elemental constituents thereof, a very intimate, preferably finely divided, dry mixture whose composition corresponds to the stoichiometry thereof, and calcining it at temperatures of 350 to 650° C. The calcination can be effected either under inert gas or under an oxidative atmosphere, for example air (mixture of inert gas and oxygen), or else under a reducing atmosphere (for example mixture of inert gas, $NH_3$, CO and/or $H_2$). The calcination time may be a few minutes to a few hours and typically decreases with temperature. Useful sources for the elemental constituents of the multimetal oxide active materials I include those compounds which are already oxides and/or those compounds which can be converted to oxides by heating, at least in the presence of oxygen.

In addition to the oxides, useful such starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be broken down to compounds which escape in gaseous form no later than in the course of the later calcining, can additionally be incorporated into the intimate dry mixture).

The intimate mixing of the starting compounds to prepare multimetal oxide active materials I can be effected in dry or wet form. When it is effected in dry form, the starting compounds are appropriately used in the form of fine powder and, after the mixing and optional compaction, subjected to calcination. Preference is given, however, to intimate mixing in wet form. This typically involves mixing the starting compounds with one another in the form of an aqueous solution and/or suspension. Particularly intimate dry mixtures are obtained in the mixing process described when the starting materials are exclusively sources of the elemental constituents present in dissolved form. The solvent used is preferably water. Subsequently, the resulting aqueous material is dried, the drying operation preferably being effected by spray-drying the aqueous mixture with exit temperatures of 100 to 150° C.

Typically, the multimetal oxide active materials of the general formula I are used in the (fresh) fixed catalyst bed for an inventive gas phase partial oxidation to acrolein not in powder form but shaped to particular catalyst geometries, in which case the shaping may precede or follow the final calcination. For example, the powder form of the active material or the uncalcined and/or partially calcined precursor material thereof can be used to produce unsupported catalysts by compacting to the desired catalyst geometry (for example by tableting or extruding), in which case it is optionally possible to add assistants, for example graphite or stearic acid as lubricants and/or shaping assistants, and reinforcing agents such as microfibers of glass, asbestos, silicon carbide or potassium titanate. Suitable unsupported catalyst geometries are, for example, solid cylinders or hollow cylinders with an external diameter and a length of 2 to 10 mm. In the case of the hollow cylinders, a wall thickness of 1 to 3 mm is appropriate. It will be appreciated that the unsupported catalyst may also have spherical geometry, in which case the sphere diameter may be 2 to 10 mm.

A particularly favorable hollow cylinder geometry is 5 mm×3 mm×2 mm (external diameter×length×internal diameter), especially in the case of unsupported catalysts.

It will be appreciated that the pulverulent active material or the pulverulent precursor material thereof, which is yet to be calcined and/or has been partially calcined, can also be shaped by application to preshaped inert catalyst supports. The coating of the support bodies to produce eggshell catalysts is generally performed in a suitable rotatable vessel, as known, for example, from DE-A 29 09 671, EP-A 293 859 or from EP-A 714 700. Appropriately, the support bodies are coated by moistening the powder material to be applied and drying it again after the application, for example by means of hot air. The layer thickness of the powder material applied to the support body is appropriately selected within the range of 10 to 1000 μm, preferably in the range of 50 to 500 μm and more preferably in the range of 150 to 250 μm.

The support materials used may be customary porous or nonporous aluminum oxides, silicon dioxide, thorium dioxide, zirconium dioxide, silicon carbide, or silicates such as magnesium or aluminum silicate. They generally behave essentially inertly with regard to the inventive target reaction. The support bodies may have a regular or irregular shape, preference being given to regular-shaped support bodies with distinct surface roughness, for example spheres or hollow cylinders. It is suitable to use essentially nonporous, spherical steatite supports with a rough surface (for example C 220 Steatite from CeramTec), the diameter of which is 1 to 8 mm, preferably 4 to 5 mm. However, it is also suitable to use cylinders as support bodies, the length of which is 2 to 10 mm and the external diameter of which is 4 to 10 mm. In the case of rings suitable in accordance with the invention as support bodies, the wall thickness is additionally typically 1 to 4 mm. Annular support bodies for use with preference in accordance with the invention have a length of 2 to 6 mm, an external diameter of 4 to 8 mm and a wall thickness of 1 to 2 mm. Support bodies suitable in accordance with the invention are in particular also rings of geometry 7 mm×3 mm×4 mm (external diameter×length×internal diameter). The fineness of the catalytically active oxide materials to be applied to the surface of the support body is of course adjusted to the desired shell thickness (cf. EP-A 714 700).

Multimetal oxide active materials suitable for the (fresh) catalysts of an inventive partial oxidation for preparation of acrolein are additionally materials of the general formula II,

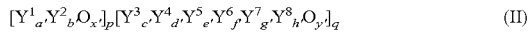

$$[Y^1_{a'}Y^2_{b'}O_{x'}]_{p'}[Y^3_{c'}Y^4_{d'}Y^5_{e'}Y^6_{f'}Y^7_{g'}Y^8_{h'}O_{y'}]_{q'} \quad (II)$$

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=nickel and/or cobalt, and optionally one or more of the elements copper, manganese, zinc, tin, cadmium, mercury and the alkaline earth metals,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum, or molybdenum and tungsten,
$a'$=0.01 to 8,
$b'$=0.1 to 30,
$c'$=0 to 4,
$d'$=0.1 to 20,
$e'$>0 to 20, preferably 0.01 or 0.1 to 20,
$f'$=0 to 6,
$g'$=0 to 15,
$h'$=8 to 16,
$x',y'$=numbers which are determined by the valency and frequency of the elements in II other than oxygen, and
$p,q$=numbers whose p/q ratio is 0.1 to 10,
comprising three-dimensional regions which are delimited from their local environment owing to their different composition than their local environment and which are of the chemical composition $Y^1_{a'}Y^2_{b'}O_{x'}$ and whose greatest diameter (longest line which goes through the center of the region and connects two points on the surface (interface) of the region) is 1 nm to 100 μm, frequently 10 nm to 500 nm or 1 μm to 50 or to 25 μm.

Particularly advantageous inventive multimetal oxide materials II are those in which $Y^1$ is only bismuth.

Among these, preference is given in turn to those which are of the general formula III,

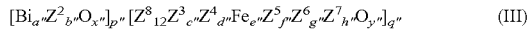

$$[Bi_{a''}Z^2_{b''}O_{x''}]_{p''}[Z^8_{12}Z^3_{c''}Z^4_{d''}Fe_{e''}Z^5_{f''}Z^6_{g''}Z^7_{h''}O_{y''}]_{q''} \quad (III)$$

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
$Z^8$=molybdenum, or molybdenum and tungsten,
$a''$=0.1 to 1,
$b''$=0.2 to 2,
$c''$=3 to 10,
$d''$=0.02 to 2,
$e''$=0.01 to 5, preferably 0.1 to 3,
$f''$=0 to 5,
$g''$=0 to 10,
$h''$=0 to 1,
$x'',y''$=numbers which are determined by the valency and frequency of the elements in III other than oxygen,
$p'',q''$=numbers whose p''/q'' ratio is 0.1 to 5, preferably 0.5 to 2, very particular preference being given to those materials III in which $Z^2{}_{b'''}=$(tungsten)$_{b'''}$ and $Z^8{}_{12}=$(molybdenum)$_{12}$.

It is additionally advantageous when at least 25 mol % (preferably at least 50 mol % and more preferably 100 mol %) of the total proportion of $[Y^1{}_a Y^2{}_b O_{x'}]_p$ ($[Bi_{a''} Z^2{}_{b''} O_{x''}]_{p''}$) of the multimetal oxide materials II (multimetal oxide materials III) suitable in accordance with the invention are present in the multimetal oxide materials II (multimetal oxide materials III) suitable in accordance with the invention in the form of three-dimensional regions which are delimited from their local environment owing to their different chemical composition than their local environment and are of the chemical composition $Y^1{}_a Y^2{}_b O_{x'}$ ($Bi_{a''} Z^2{}_{b''} O_{x''}$) and whose greatest diameter is in the range of 1 nm to 100 μm.

With regard to the shaping, the statements made for the multimetal oxide material I catalysts apply with regard to multimetal oxide material II catalysts.

The preparation of multimetal oxide material II active materials is described, for example, in DE application 102008054586.4, DE-A 102008040093, DE-A 102008040094, EP-A 575 897 and in DE-A 198 55 913.

The inert support materials recommended above are also options, inter alia, as inert materials for dilution and/or delimitation of the appropriate fixed catalyst bed, or as the protective preliminary bed thereof.

Appropriately in application terms, the process according to the invention is performed in a thermoplate reactor (cf., for example, DE-A 10 2004 017150) or in a tube bundle reactor (cf., for example, WO 2005/042459 and WO 2007/082827). Preference is given in accordance with the invention to performance in a tube bundle reactor. In this case, the fixed catalyst bed is present in the simplest case in the metal tubes of the tube bundle reactor, and a temperature medium (one-zone method), generally a salt melt (preferably composed of 60% by weight of potassium nitrate and 40% by weight of sodium nitrite) is conducted around the metal tubes. Salt melt and reaction gas mixture can be conducted in simple cocurrent or countercurrent. However, the salt melt (the heat carrier, the heating medium) may also be conducted around the tube bundle in a meandering manner viewed over the reactor, such that only viewed over the entire reactor does a cocurrent or countercurrent flow exist with respect to the flow direction of the reaction gas mixture. The flow rate of the heating medium (heat carrier, heat exchange medium) is typically such that the temperature rise (caused by the exothermicity of the reaction) of the heat exchange medium from the inlet point into the reactor to the outlet point out of the reactor is $\geq 0$ to 10° C., frequently $\geq 2$ to 8° C. and often $\geq 3$ to 6° C. The inlet temperature of the heat carrier into the tube bundle reactor will, in an inventive heterogeneously catalyzed gas phase partial oxidation process, generally be 250 to 390° C., frequently 280 to 360° C. or 300 to 340° C.

Suitable heat carriers are especially melts of salts such as potassium nitrate, potassium nitrite, sodium nitrite and/or sodium nitrate, or of low-melting metals such as sodium, mercury, and alloys of different metals. As already mentioned, the process according to the invention, especially in the case of comparatively elevated loadings of the fixed catalyst bed with the at least one organic precursor compound to be partially oxidized (e.g. $\geq 130$ l (STP)/l·h, or $\geq 160$ l (STP)/l·h, or $\geq 180$ l (STP)/l·h, or $\geq 200$ l (STP)/l·h; but usually $\leq 600$ l (STP)/l·h or $\leq 300$ l (STP)/l·h), for example propylene, is performed in a two-zone tube bundle reactor (or generally multizone tube bundle reactor). A preferred variant of a two-zone tube bundle reactor useable in accordance with the invention is disclosed by DE-C 2830765. However, the two-zone tube bundle reactors disclosed in DE-C 2513405, U.S. Pat. No. 3,147,084, DE-A 2201528, EP-A 383224, DE-A 2903218 and WO 2004/085369 are also suitable.

In other words, in the simplest manner, the fixed catalyst bed for use is present here too in the metal tubes of a tube bundle reactor. However, two essentially spatially separate heating media (heat carriers), generally salt melts, are conducted around the metal tubes. The tube section over which the particular salt bath extends represents one reaction zone or else temperature zone. For example, a salt bath A preferably flows around that section of the tubes (the temperature zone A) in which, for example, the oxidative conversion of the propylene, for example, (in the case of single pass of the reaction gas mixture) proceeds until a conversion in the range from 40 to 80 mol % is attained, and a salt bath B flows around, for example, the section of the tubes (the temperature zone B) in which, for example, the oxidative further conversion of the propylene, for example, (in single pass of the reaction gas mixture) proceeds until a conversion value of $\geq 90$ mol % is attained (if required, the reaction zones A, B may be followed by further reaction zones which are kept at individual temperatures).

Within the particular temperature zone, the salt bath can be conducted as in the one-zone method. The feed temperature of the salt bath B is normally at least 5° C. above the temperature of the salt bath A.

Otherwise, the two-zone method can be carried out as in WO 2007/082827 and the prior art acknowledged in this document.

The determination of the temperature of the reaction gas mixture in the course of reactive flow through the fixed catalyst bed can be effected in a simple manner, for example with the aid of thermocouples which are introduced into the fixed catalyst bed. The procedure may, for example, be as described in WO 2005/005037, or in EP-A 1 270 065, or in DE-A 19717165, or in DE-A 10361515. In the simplest case, a thermowell is conducted through the fixed catalyst bed. The thermocouple (which is optionally a multiple thermocouple) is conducted therein, and can be used to gauge the temperature of the fixed catalyst bed. Alternatively, the reaction temperature profile in the fixed catalyst bed can, however, also be determined by calculation with the aid of heat of reaction, conversion, the relevant heat transfer and heat passage coefficients, and knowledge of the fixed catalyst bed.

The conversion can be determined along the fixed catalyst bed either experimentally or on the basis of reaction kinetics models.

The volume-specific activity of the fixed catalyst bed (cf. DE-A 10 2006 000996) in the process according to the invention can be configured to increase or decrease either constantly or in flow direction of the fixed catalyst bed over the length of the fixed catalyst bed (cf. WO 2007/082827). Advantageously in accordance with the invention, the volume-specific activity of the fixed catalyst bed is configured to increase in flow direction of the reaction gas mixture. In a simple manner, this can be accomplished by decreasing dilution of the fixed catalyst bed with inert shaped bodies in flow direction of the reaction gas mixture.

For the determination of particle diameters $d_{50}{}^M$ (or $d_x{}^M$ in general) in the examples and comparative examples which follow, the particular finely divided mixture (M) was conducted via a dispersing channel into the Sympatec RODOS dry disperser (Sympatec GmbH, System-Partikel-Technik, Am Pulverhaus 1, D-38678 Clausthal-Zellerfeld) and dry-dispersed there with compressed air and blown into the test cell in a free jet. The volume-based particle diameter distribution was then determined therein to ISO 13320 with the Malvern Mastersizer S laser diffraction spectrometer (Malvern Instruments, Worcestershire WR14 1AT, United Kingdom). The particle diameters $d_x^M$ reported as the measurement result are defined such that X% of the total particle volume of the finely divided mixture (M) consists of particles with this or a smaller diameter.

This means that (100−X)% of the aforementioned total particle volume consists of particles with a diameter >$d_x^M$. Unless explicitly stated otherwise in this document, particle diameter determinations on finely divided mixtures (M) and $d_x^M$ inferred therefrom always relate to the above-described determination method and to a dispersion pressure of 2 bar absolute (which determines the extent of dispersion of the powder during the measurement) employed in the determination.

In this document, the term "multielement oxide" does not mean a simple mixture of different element oxides, but rather a complex polyoxy compound.

When semimetals such as phosphorus, antimony, arsenic and silicon are counted among the metals in this document, the multielement oxide active materials for use in accordance with the invention are generally multimetal oxides. In principle, the multielement oxide active materials for use in accordance with the invention may, however, also comprise nonmetals, for example the element sulfur.

When the heterogeneously catalyzed partial gas phase oxidation to prepare (meth)acrolein is performed in a tube bundle reactor, the reaction tubes of which have been charged with a fresh fixed catalyst bed suitable for the performance of the process according to the invention, it is advantageous when the process for gas phase partial oxidation in the first 8000 operating hours is performed in accordance with the invention in at least 50%, preferably in at least 60%, more preferably in at least 70%, preferably in at least 80%, even more preferably in at least 90% and best in 100% of the total number of reaction tubes present in the tube bundle reactor. This is generally ensured when the heat transfer from the reaction tube to the heat carrier conducted through the tube bundle reactor is the same for all reaction tubes present in the tube bundle reactor.

The present patent application thus comprises especially the following embodiments of the invention:

1. A process for preparing (meth)acrolein by heterogeneously catalyzed gas phase partial oxidation, in which a reaction gas mixture is passed at elevated temperature through a fresh fixed catalyst bed present in a reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst bed is at least one multielement oxide which comprises the elements Mo, Fe and Bi and additionally at least one of the two elements Ni and Co, wherein the process, over the first 8000 operating hours of the fresh fixed catalyst bed, during which the reaction gas mixture supplied to the fixed catalyst bed at a loading of the fixed catalyst bed with the organic precursor compound of at least 40 l (STP)/l·h comprises at least 3% by volume of the organic precursor compound to be partially oxidized and, based on a single pass of the reaction gas mixture through the fixed catalyst bed, at least 90 mol % of the organic precursor compound present therein is converted and the highest temperature $T^H$ of the reaction gas mixture in the course of passage through the fixed catalyst bed is at least 300° C., is performed such that, during X=10 to 500 operating hours, the highest temperature $T^H$ of the reaction gas mixture as it passes through the fixed catalyst bed is 400 to 450° C. and, during the remaining 8000-X operating hours, is less than 400° C., and the loading of the fixed catalyst bed with the at least one organic precursor compound to be partially oxidized, averaged arithmetically over the time, for the X operating hours is greater than for the 8000-X operating hours.

2. The process according to embodiment 1, wherein X=20 to 450 operating hours.
3. The process according to embodiment 1, wherein X=30 to 400 operating hours.
4. The process according to embodiment 1, wherein X=50 to 300 operating hours.
5. The process according to embodiment 1, wherein X=75 to 275 operating hours.
6. The process according to any of embodiments 1 to 5, wherein $T^H$ during the X operating hours is 405 to 445° C.
7. The process according to any of embodiments 1 to 5, wherein $T^H$ during the X operating hours is 405 to 440° C.
8. The process according to any of embodiments 1 to 5, wherein $T^H$ during the X operating hours is 410 to 435° C.
9. The process according to any of embodiments 1 to 5, wherein $T^H$ during the X operating hours is 410 to 430° C. or 400 to 420° C.
10. The process according to any of embodiments 1 to 9, wherein $T^H$ during the 8000-X operating hours is 300 to 399° C.
11. The process according to any of embodiments 1 to 9, wherein $T^H$ during the 8000-X operating hours is 300 to 398° C.
12. The process according to any of embodiments 1 to 9, wherein $T^H$ during the 8000-X operating hours is 300 to 395° C.
13. The process according to any of embodiments 1 to 9, wherein $T^H$ during the 8000-X operating hours is 310 to 390° C.
14. The process according to any of embodiments 1 to 9, wherein $T^H$ during the 8000-X operating hours is 320 to 385° C.
15. The process according to any of embodiments 1 to 9, wherein $T^H$ during the 8000-X operating hours is 330 to 380° C.
16. The process according to any of embodiments 1 to 9, wherein $T^H$ during the 8000-X operating hours is 340 to 370° C.
17. The process according to any of embodiments 1 to 16, wherein, during at least 20% of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000-X operating hours.
18. The process according to any of embodiments 1 to 16, wherein, during at least 60% of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000-X operating hours.
19. The process according to any of embodiments 1 to 16, wherein, during at least 80% of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000−X operating hours.
20. The process according to any of embodiments 1 to 16, wherein, during the entire duration of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000−X operating hours.
21. The process according to any of embodiments 1 to 20, wherein the loading of the fixed catalyst bed with the at least one organic precursor compound to be partially oxidized, averaged arithmetically over the time, for the X operating hours is at least 5 to 60% or at least 10 to 60% greater than for the 8000−X operating hours.
22. The process according to any of embodiments 1 to 20, wherein the loading of the fixed catalyst bed with the at least one organic precursor compound to be partially oxidized, averaged arithmetically over the time, for the X operating hours is at least 20% or at least 40% greater than for the 8000−X operating hours.
23. The process according to any of embodiments 1 to 20, wherein the loading of the fixed catalyst bed with the at least one organic precursor compound to be partially oxidized, averaged arithmetically over the time, for the X operating hours is at least 60% greater than for the 8000−X operating hours.
24. The process according to any of embodiments 1 to 20, wherein the loading of the fixed catalyst bed with the at least one organic precursor compound to be partially oxidized, averaged arithmetically over the time, for the X operating hours is at least 80% greater than for the 8000−X operating hours.
25. The process according to any of embodiments 1 to 24, wherein the loading of the fixed catalyst bed with the at least one organic precursor compound to be partially oxidized, averaged arithmetically over the time, for the X operating hours is not more than 300%, or not more than 200%, or not more than 100%, above that for the 8000−X operating hours.
26. The process according to any of embodiments 1 to 26, wherein the loadings of the fixed catalyst bed with the at least one organic precursor compound to be partially oxidized employed during the X operating hours differ by not more than ±40 l (STP)/l·h or by not more than ±20 l (STP)/l·h from the arithmetic mean thereof formed over the X operating hours.
27. The process according to any of embodiments 1 to 26, wherein the loadings of the fixed catalyst bed with the at least one organic precursor compound to be partially oxidized employed during the 8000−X operating hours differ by not more than ±40 l (STP)/l·h or by not more than ±20 l (STP)/l·h from the arithmetic mean thereof formed over the 8000−X operating hours.
28. The process according to any of embodiments 1 to 27, wherein the total number of the X operating hours is within the first 7000 operating hours.
29. The process according to any of embodiments 1 to 27, wherein the total number of the X operating hours is within the first 6000 operating hours.
30. The process according to any of embodiments 1 to 27, wherein the total number of the X operating hours is within the first 5000 operating hours.
31. The process according to any of embodiments 1 to 27, wherein the total number of the X operating hours is within the first 4000 operating hours.
32. The process according to any of embodiments 1 to 27, wherein the total number of the X operating hours is within the first 3000 operating hours.
33. The process according to any of embodiments 1 to 32, wherein the total number of the X operating hours is within the first 2000 operating hours.
34. The process according to any of embodiments 1 to 32, wherein the total number of the X operating hours is within the first 1000 operating hours or within the first 700 operating hours.
35. The process according to any of embodiments 1 to 34, wherein, based on a single pass of the reaction gas mixture through the fixed catalyst bed, at least 92 mol % of the organic precursor compound present therein is converted.
36. The process according to any of embodiments 1 to 34, wherein, based on a single pass of the reaction gas mixture through the fixed catalyst bed, at least 94 mol % of the organic precursor compound present therein is converted.
37. The process according to any of embodiments 1 to 34, wherein, based on a single pass of the reaction gas mixture through the fixed catalyst bed, at least 96 mol % of the organic precursor compound present therein is converted.
38. The process according to any of embodiments 1 to 37, wherein, based on a single pass of the reaction gas mixture through the fixed catalyst bed, ≦99 mol % of the organic precursor compound present therein is converted.
39. The process according to any of embodiments 1 to 38, wherein the product gas mixture during the X operating hours still comprises at least 0.1% by volume of the at least one organic precursor compound to be partially oxidized.
40. The process according to any of embodiments 1 to 38, wherein the product gas mixture during the X operating hours still comprises at least 0.3% by volume of the at least one organic precursor compound to be partially oxidized.
41. The process according to any of embodiments 1 to 38, wherein the product gas mixture during the X operating hours still comprises at least 0.5% by volume of the at least one organic precursor compound to be partially oxidized.
42. The process according to any of embodiments 1 to 41, wherein the product gas mixture during the X operating hours comprises ≦1% by volume of the at least one organic precursor compound to be partially oxidized.
43. The process according to any of embodiments 1 to 42, wherein the loading of the fixed catalyst bed with the at least one organic precursor compound to be partially oxidized during the first 8000 operating hours is ≧50 to ≦300 l (STP)/l·h.
44. The process according to any of embodiments 1 to 42, wherein the loading of the fixed catalyst bed with the at least one organic precursor compound to be partially oxidized during the first 8000 operating hours is ≧75 to ≦250 l (STP)/l·h.
45. The process according to any of embodiments 1 to 42, wherein the loading of the fixed catalyst bed with the at least one organic precursor compound to be partially oxidized during the first 8000 operating hours is ≧80 to ≦200 l (STP)/l·h or 90 to ≦150 l (STP)/l·h.
46. The process according to any of embodiments 1 to 45, wherein the molar ratio V of $O_2$:organic precursor compound in the reaction gas mixture supplied to the fixed catalyst bed is ≧1 and ≦3.
47. The process according to embodiment 46, wherein the molar ratio V is ≧1.5 and ≦2.0.
48. The process according to any of embodiments 1 to 45, wherein the molar ratio V of $O_2$:organic precursor compound in the reaction gas mixture supplied to the fixed catalyst bed during the X operating hours is ≧1 and ≦1.5.

49. The process according to embodiment 48, wherein V during the X operating hours is $\geq 1.10$ and $\leq 1.40$.
50. The process according to embodiment 48, wherein V during the X operating hours is $\geq 1.20$ and $\leq 1.40$.
51. The process according to any of embodiments 1 to 50, wherein the molar ratio V of $O_2$ to organic precursor compound in the reaction gas mixture supplied to the fixed catalyst bed during the 8000–X operating hours is $\geq 1.5$ and $\leq 3$.
52. The process according to any of embodiments 1 to 51, wherein the proportion A of the at least one organic precursor compound to be partially oxidized in the reaction gas mixture supplied to the fixed catalyst bed is $\geq 4\%$ by volume and $\leq 15\%$ by volume.
53. The process according to embodiment 52, wherein the proportion A is $\geq 5\%$ by volume and $\leq 12\%$ by volume.
54. The process according to any of embodiments 1 to 53, wherein the at least one organic precursor compound is propylene or isobutene.
55. The process according to any of embodiments 1 to 54, wherein the active material of the catalysts of the fixed catalyst bed is at least one multielement oxide of the general formula I $$Mo_{12}Bi_aFe_bX^1_cX^2_dX^3_eX^4_fO_n \quad (I),$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.05 to 5,
b=0.01 to 5, preferably 2 to 4,
c=0.1 to 10, preferably 3 to 10,
d=0 to 2, preferably 0.02 to 2,
e=0 to 8, preferably 0 to 5,
f=0 to 10 and
n=a number which is determined by the valency and frequency of the elements in I other than oxygen.
56. The process according to any of embodiments 1 to 54, wherein the active material of the catalysts of the fixed catalyst bed is at least one multielement oxide of the general formula II $$[Y^1_{a'}Y^2_{b'}O_{x'}]_p[Y^3_{c'}Y^4_{d'}Y^5_{e'}Y^6_{f'}Y^7_{g'}Y^8_{h'}O_{y'}]_q \quad (II),$$

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=nickel and/or cobalt, and optionally one or more of the elements copper, manganese, zinc, tin, cadmium, mercury and the alkaline earth metals,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$Y^8$=molybdenum, or molybdenum and tungsten,
a'=0.01 to 8,
b'=0.1 to 30,
c'=0 to 4,
d'=0.1 to 20,
e'>0 to 20, preferably 0.01 or 0.1 to 20,
f'=0 to 6,
g'=0 to 15,
h'=8 to 16,
x',y'=numbers which are determined by the valency and frequency of the elements in II other than oxygen, and
p,q=numbers whose p/q ratio is 0.1 to 10,
comprising three-dimensional regions which are delimited from their local environment owing to their different composition than their local environment and which are of the chemical composition $Y^1_aY^2_bO_{x'}$ and whose greatest diameter is 1 nm to 100 μm.
57. The process according to any of embodiments 1 to 56, wherein the fixed catalyst bed is present in a reaction tube of a tube bundle reactor.
58. A process for preparing (meth)acrolein by heterogeneously catalyzed gas phase partial oxidation of at least one organic precursor compound to be partially oxidized, in which a reaction gas mixture is passed at elevated temperature through the fresh fixed catalyst beds present in the reaction tubes of a tube bundle reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst beds is at least one multielement oxide which comprises the elements Mo, Fe and Bi and additionally at least one of the two elements Ni and Co, wherein, in the first 8000 operating hours of the fresh fixed catalyst beds, the process in at least 50% of the reaction tubes present in the tube bundle reactor is a process according to any of embodiments 1 to 57.
59. The process according to embodiment 58, wherein, in the first 8000 operating hours of the fresh fixed catalyst bed, the process in at least 70% of the reaction tubes present in the tube bundle reactor is a process according to any of embodiments 1 to 57.
60. The process according to embodiment 58, wherein, in the first 8000 operating hours of the fresh fixed catalyst bed, the process in at least 90% of the reaction tubes present in the tube bundle reactor is a process according to any of embodiments 1 to 57.
61. The process according to embodiment 58, wherein, in the first 8000 operating hours of the fresh fixed catalyst bed, the process in all of the reaction tubes present in the tube bundle reactor is a process according to any of embodiments 1 to 57.
62. The process according to any of embodiments 1 to 61, wherein the partial pressure of the at least one organic precursor compound in the reaction gas mixture supplied to the fixed catalyst bed during the X operating hours is above the corresponding partial pressure of the at least one organic precursor compound during the 8000–X operating hours.

EXAMPLES AND COMPARATIVE EXAMPLES

I) Preparation of Annular Unsupported Catalysts I with the Following Stoichiometry of the Active Material: $[Bi_2W_2O_9 \bullet 2\ WO_3]_{0.40}[Mo_{12}Co_{5.4}Fe_{3.1}Si_{1.5}K_{0.08}O_x]_1$.

a) Preparation of the Starting Material 1 ($Bi_1W_2O_{7.5}=\frac{1}{2}Bi_2W_2O_9 \bullet 1\ WO_3$)

In a 1.75 m³ stainless steel jacketed vessel (for temperature control water flowed through the interspace) with a cross-beam stirrer, 214.7 kg of tungstic acid at 25° C. (74.1% by weight of W, mean particle size (according to manufacturer determined to ASTM B 330) from 0.4 to 0.8 μm, ignition loss (2 h at 750° C. under air) 6-8% by weight, D-38615 Goslar) were stirred (70 rpm) in portions into 780 kg of an aqueous bismuth nitrate solution in nitric acid at 25° C. (11.2% by weight of Bi; free nitric acid: 3 to 5% by weight; prepared with nitric acid from bismuth metal from Sidech S.A., 1495 Tilly, Belgium, purity: >99.997% by weight of Bi, <7 mg/kg of Pb, <5 mg/kg each of Ni, Ag, Fe, <3 mg/kg each of Cu, Sb, and <1 mg/kg each of Cd, Zn) at 25° C. within 20 min. The resulting aqueous mixture was then stirred at 25° C. for another 3 h and then spray-dried. The spray-drying was effected in a Niro FS 15 rotary-disk spray tower in hot air cocurrent at a gas inlet temperature of 300±10° C., a gas outlet temperature of 100±10° C., a disk speed of 18 000 rpm, a throughput of 200 l/h and an air rate of 1800 m$^3$ (STP)/h. During the spray drying, the stirring was continued at 25° C. in the proportion of the aqueous mixture which was yet to be spray-dried. The resulting spray powder had an ignition loss of 12.8% by weight (calcine under air at 600° C. for 3 h in a porcelain crucible (which had been calcined to constant weight at 900° C.)) and had (at a dispersion pressure of 1.1 bar absolute) a $d_m$ of 28.0 μm ($d_{10}$=9.1 μm, $d_{90}$=55.2 μm).

The resulting spray powder was subsequently converted to a paste with 16.7% by weight (based on the powder) of water at 25° C. in a discharging kneader for 30 min, and kneaded at a speed of 20 rpm and extruded by means of an extruder to extrudates of diameter 6 mm. These were cut into 6 cm sections, dried under air on a 3-zone belt dryer with a residence time of 40 min per zone at temperatures of 90-95° C. (zone 1), 115° C. (zone 2) and 125° C. (zone 3), and then treated thermally at a temperature in the region of 830° C. (calcined; in a rotary tube oven with air flow (reduced pressure 0.3 mbar, 200 m$^3$ (STP)/h of air, 50 kg/h of extrudate, speed: 1 rpm)). What is important in the exact setting of the calcination temperature is that it has to be oriented to the desired phase composition of the calcination product, but, on the other hand, the calcined material has a BET surface area of 0.2 m$^2$/g. The desired phases are $WO_3$ (monoclinic) and $Bi_2W_2O_9$ (orthorhombic); what is undesired here is the presence of γ-$Bi_2WO_6$ (russellite). Should the content of the γ-$Bi_2WO_6$ compound after the calcination be more than 5 intensity % (calculated as the ratio (int. r.) of the intensity of the reflection of γ-$Bi_2WO_6$ in the X-ray powder diffractogram at 2Θ=28.4° (CuKα radiation) to the intensity of the reflection of $Bi_2W_2O_9$ at 2Θ=30.0°), the preparation should therefore be repeated and the calcination temperature or the residence time at the same calcination temperature should be increased until the value attains or goes below the limit. The preformed calcined mixed oxide thus obtained was ground with a 500 BQ biplex crossflow classifying mill from Hosokawa Alpine AG, Augsburg, at 2500 rpm, such that the $d_{50}{}^{41}$ value of the finely divided starting material 1 was 2.8 μm (measured at a dispersion pressure of 2.0 bar absolute), the BET surface area was 0.6 m$^2$/g (measured by nitrogen adsorption after activation under reduced pressure at 200° C. for 4 h) and the γ-$Bi_2WO_6$ content was 2 intensity % (=100%●in r.). Before the further processing described under c), the finely divided starting material A1 was mixed in portions of 20 kg each in a tilted mixer with mixing and cutting blades (mixing blade speed: 60 rpm, cutting blade speed: 3000 rpm) homogeneously with 0.5% by weight (based on the particular finely divided starting material A1) of Sipernat® D17 finely divided hydrophobized $SiO_2$ from Degussa (tapped density: 150 g/l; $d_{50}$ = 10 μm of the $SiO_2$ particles (laser diffraction to ISO 13320-1)=10 μm, the specific surface area (nitrogen adsorption to ISO 5794-1, Annex D)=100 m$^2$/g) as an anticaking agent within 5 min.

b) Preparation of the Starting Material 2 ($Mo_{12}Co_{5.4}Fe_{3.1}Si_{1.5}K_{0.08}O_x$)

A solution A was prepared by metering 1.075 kg of an aqueous potassium hydroxide solution (47.5% by weight KOH) at a temperature of 60° C. and subsequently, via a differential metering balance at a metering rate of 600 kg/h, 237.1 kg of ammonium heptamolybdate tetrahydrate at a temperature of 25° C. (white crystals with a particle size d of <1 mm, 81.5% by weight of $MoO_3$, 7.0-8.5% by weight of $NH_3$, max. 150 mg/kg of alkali metals, H.C. Starck, D-38642 Goslar) into 660 l of water at a temperature of 60° C. in a water-heated 1.75 m$^3$ stainless steel jacketed vessel with a crossbeam stirrer at 60° C. with stirring (70 rpm) within one minute, and the resulting solution was stirred at 60° C. for 60 min (70 rpm).

A solution B was prepared by initially charging a water-heated 1.75 m$^3$ stainless steel jacketed vessel with a crossbeam stirrer at 60° C. with 282.0 kg of an aqueous cobalt(II) nitrate solution at a temperature of 60° C. (12.5% by weight of Co, prepared with nitric acid from cobalt metal from MFT Metals & Ferro-Alloys Trading GmbH, D-41747 Viersen, purity >99.6% by weight, <0.3% by weight of Ni, <100 mg/kg of Fe, <50 mg/kg of Cu), and 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal) were metered into it with stirring (70 rpm). Subsequently, the mixture was stirred for a further 30 minutes while maintaining the 60° C. Then, while maintaining the 60° C., solution B was discharged into the initially charged solution A and stirred at 70 rpm at 60° C. for a further 15 minutes. Subsequently, 19.9 kg of a Ludox TM 50 silica sol from Grace at 25° C. (50.1% by weight of $SiO_2$, density: 1.29 g/ml, pH 8.5 to 9.5, alkali metal content max. 0.5% by weight) were added to the resulting aqueous mixture which was then stirred at 70 rpm at 60° C. for a further 15 minutes. This was followed by spray-drying in a Niro FS-15 rotary-disk spray tower in hot air countercurrent at a disk speed of 18 000 rpm (gas inlet temperature: 350±10° C., gas outlet temperature: 140±5° C., throughput: 270 kg/h). During the spray drying, the stirring was continued at 60° C. in the proportion of the aqueous mixture which was yet to be spray-dried. The resulting spray powder had an ignition loss of 31% by weight (calcine under air at 600° C. for 3 h in a porcelain crucible (which had been calcined to constant weight at 900° C.)) and had (at a dispersion pressure of 1.1 bar absolute) a $d_{50}$ of 33.0 μm.

c) Production of the Annular Unsupported Catalysts I from the Starting Materials 1 and 2

110 kg of starting material 2 were then initially charged in a tilted mixer (VIL type, fill volume: 200 l, Aachener Misch- und Knetmaschinenfabrik) with mixing and cutting blades (mixing blade speed: 39 rpm, cutting blade speed: 3000 rpm) and premixed for 1 min. Within 10 min, with continued mixing, via a star feeder, starting material 1 was metered thereto in the amount required for a multimetal oxide active material of stoichiometry:

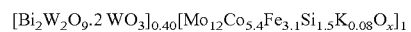

$[Bi_2W_2O_9 \cdot 2\ WO_3]_{0.40}[Mo_{12}Co_{5.4}Fe_{3.1}Si_{1.5}K_{0.08}O_x]_1$ within 10 min. The mixing operation was then continued for a further 15 min in order to achieve an intensive and complete homogenization (including the breaking apart of any agglomerates present) of the two starting materials (which is required to achieve a high activity and high acrolein selectivity). Based on the aforementioned overall composition, 1% by weight of TIMREX T44 graphite from Timcal AG was mixed in within a further 2 min.

The resulting mixture was then compacted in a K200/100 compactor from Hosokawa Bepex GmbH with concave, fluted smooth rollers (gap width: 2.8 mm, roller speed: 9 rpm, target pressing force: approx. 75 kN). Integrated vibrating screens from Allgaier (oversize screen size: 1.5 mm, undersize screen size: 400 µm) with ball-type screening aids (diameter 22 mm) were used to isolate a compactate having a particle size for the most part between 400 µm and 1.5 mm.

For the tableting, a further 2.5% by weight of the TIMREX T44 graphite from Timcal AG were added to the compactate in a turbulent mixer from Drais over the course of 2 minutes.

Subsequently, the pulverulent aggregate obtained as described was compacted as described in DE-A 102008040093 under an air atmosphere with the aid of a Korsch PH 865 rotary press (single mold, 65 dies). The diameter of the preliminary pressure roller was 100 mm and the diameter of the main pressure roller was 300 mm. The distance between two dies opposite one another on the die table was 780 mm. The side crushing strengths of the resulting ringlike (5 mm×3 mm×2 mm=external diameter×height×internal diameter) shaped multimetal oxide unsupported catalyst precursor bodies with a planar end face were in the range from 21 to 23 N. The rotation rate of the rotary press was from 35 to 45 rpm.

Subsequently, the ringlike shaped multimetal oxide unsupported catalyst precursor bodies produced were, as described in example 1 of DE-A 100 46 957 (except that the bed height in the decomposition (chambers 1 to 4) was 53 mm with a residence time per chamber of 1.23 h and, in the calcination (chambers 5 to 8) it was 130 mm with a residence time of 3.89 h), treated thermally by means of a belt calcining apparatus; the chambers had a base area (with a uniform chamber length of 1.40 m) of 1.29 m$^2$ (decomposition) and 1.40 m$^2$ (calcination), and were flowed through from below through the coarse-mesh belt by 50-210 m$^3$ (STP)/h of feed air preheated to 100° C. (decomposition) or 450° C. (calcination); in addition, the air was circulated by rotating ventilators (900 to 1450 rpm). Within the chambers, the deviation of the temperature from the target value in terms of time and location (typical values for zones 1 to 8 are: 140° C., 190° C., 220° C., 265° C., 380° C., 425° C., 460° C., 460° C.) was always ≦2° C. Beyond chamber 8, there followed a cooling zone of length 2 m, whose temperature was controlled to 70° C. Otherwise, the procedure was as described in example 1 of DE-A 100 46 957. As a result, ringlike multimetal oxide unsupported catalysts I were obtained.

III. Production of Ringlike Multimetal Oxide Unsupported Catalysts II where the Active Multimetal Oxide had the Stoichiometry $Mo_{12}Co_7Fe_3Bi_{0.6}Si_{1.6}K_{0.08}O_x$ At 60° C., 139.7 kg of ammonium heptamolybdate tetrahydrate (81.5% by weight of MoO$_3$) were dissolved in 432 l of water. While maintaining the 60° C., 0.69 kg of an aqueous potassium hydroxide solution (47.5% KOH) at 20° C. was stirred into this solution (to obtain a solution A).

A second solution, B, was prepared by adding, at 60° C., 80 kg of an iron(III) nitrate nonahydrate melt (13.8% by weight of Fe, <0.4% by weight of alkali metals, <0.01% by weight of chloride, <0.02% by weight of sulfate, Dr. Paul Lohmann GmbH, D-81857 Emmerthal) at 60° C. while stirring to 206 kg of an aqueous cobalt(II) nitrate solution (12.5% by weight of Co). After the addition had ended, stirring was continued at 60° C. for another 30 min. Thereafter, 70 kg of an aqueous bismuth nitrate solution (11.2% by weight of Bi; free nitric acid 3 to 5% by weight; prepared with nitric acid from bismuth metal from Sidech S.A., 1495 Tilly, Belgium, purity: >99,997% by weight of Bi, <7 mg/kg of Pb, <5 mg/kg each of Ni, Ag, Fe, <3 mg/kg each of Cu, Sb, and <1 mg/kg each of Cd, Zn) at 20° C. were stirred in at 60° C. to obtain solution B. Within 15 min, solution B was stirred into solution A at 60° C. 15 min after the stirring-in had ended, 9 l of silica sol of the Ludox TM-50 type (50.1% by weight of SiO$_2$, density: 1.29 g/ml, pH 8.5 to 9.5, alkali metal content max. 0.5% by weight, from Grace GmbH in D-67547 Worms) were added at 60° C. to the slurry obtained. While maintaining the 60° C., stirring was continued for another 15 min. The resulting slurry was then spray-dried in a hot air countercurrent process (gas inlet temperature: 310±10° C., gas outlet temperature: 140±5° C., throughput: 270 kg of slurry/h) to obtain a spray powder whose ignition loss (3 h at 600° C. under air) was 30% of its weight. The spray powder had a d$_{50}$ of 20.3 µm (measured at a dispersion pressure of 2 bar absolute). During the spray drying, the stirring was continued at 60° C. in the proportion of the aqueous slurry which was yet to be spray-dried.

An additional 1.0% by weight (based on the amount of spray powder) of Asbury 3160 graphite from Asbury Graphite Mills Inc., New Jersey 08802, USA, was mixed into the spray powder.

The dry mixture resulting in this case was coarsened by means of a K200/100 compactor from Hosokawa Bepex GmbH (D-74211 Leingarten) under the conditions of gap width 2.8 mm, screen width 1.0 mm, undersize screen size 200 µm, target pressing force 35 kN and screw speed 65 to 70 rpm, by preliminary compaction to an essentially uniform particle size of from 200 µm to 1 mm.

The compactate was subsequently mixed with, based on its weight, a further 2% by weight of the same graphite and then compacted with the aid of a Kilian RX 73 rotary press from Kilian, D-50735 Cologne, under an air atmosphere as described in DE-A 102008040093 to give ringlike shaped multimetal oxide unsupported catalyst precursor bodies (5 mm×3 mm×2 mm=external diameter×height×internal diameter) with an uncurved (i.e. with a planar) end face. The side crushing strength of the resulting ringlike shaped multimetal oxide precursor bodies was from 19 to 21 N.

Subsequently, the ringlike shaped multimetal oxide unsupported catalyst precursor bodies prepared were treated thermally by means of a belt calcining apparatus as described in example 1 of DE-A 100 46 957 (except that the bed height in the decomposition (chambers 1 to 4) was 25 mm with a residence time per chamber of 1.8 h, and that in the calcination (chambers 5 to 8) was 55 mm with a residence time of 4.7 h); the chambers had a base area (with a uniform chamber length of 1.40 m) of 1.29 m$^2$ (decomposition) and 1.40 m$^2$ (calcination), and were flowed through from below through the coarse-mesh belt by 50-210 m$^3$ (STP)/h of feed air preheated to 100° C. (decomposition) or 475° C. (calcination); in addition, the air was circulated by rotating ventilators (900 to 1450 rpm). Within the chambers, the deviation of the temperature from the target value in terms of time and location (typical values for zones 1-8 are: 155° C., 190° C., 220° C., 265° C., 380° C., 430° C., 500° C., 500° C.) was always ≦2° C. Beyond chamber 8 followed a 2 m-long cooling zone heated to 70° C. Otherwise, the procedure was as described in example 1 of DE-A 100 46 957. As a result, ringlike multimetal oxide unsupported catalysts II were obtained.

III. Process For Preparation of Acrolein by Heterogeneously Catalyzed Gas Phase Partial Oxidation of Propylene A reaction tube (V2A steel; external diameter 21 mm; wall thickness 3 mm, internal diameter 15 mm, length 120 cm) was charged from the top downward in each case as follows:

Section 1: Length 30 cm
  40 g of steatite spheres (C220 Steatite from CeramTec) with a diameter of 1.5 to 2.0 mm as a preliminary bed (heating zone).

Section 2: Length 70 cm
  A homogeneous mixture of 90 g of the particular fresh ringlike unsupported catalyst I or II and 10 g of steatite rings (C220 from CeramTec) of the same geometry as the particular unsupported catalyst as a fixed catalyst bed.

The temperature of the reaction tube was in each case controlled by means of a molecular nitrogen-sparged salt bath having the salt bath temperature $T^{SB}$ (° C.) required in each case (53% by weight of potassium nitrate, 40% by weight of sodium nitrite and 7% by weight of sodium nitrate). The salt bath was within a cylindrical shell of internal diameter 15 mm. The cylindrical shell had the same length as the reaction tube. The latter was conducted from the top downward within the cylindrical shell such that the two axes of symmetry coincided. The nitrogen stream sparged into the salt bath from the bottom was 40 l (STP)/h. The heat losses of the salt bath to the environment were greater than the heat of reaction produced by the reactor during the partial oxidation. The salt bath was therefore held at its temperature $T^{SB}$ (° C.) by means of electrical heating. In this way, it was ensured that the outer wall of the reaction tube always had the appropriate temperature $T^{SB}$ (° C.).

During the performance of the gas phase partial oxidation, a reaction gas input mixture (charge gas mixture of air, polymer grade propylene and molecular nitrogen) was passed through each reaction tube from the top downward and had the following composition:

5% by volume of propylene (polymer grade),
9.5% by volume of molecular oxygen, and
85.5% by volume of $N_2$.

The inlet temperature of the reaction gas mixture into the reaction tube was always 30° C. The temperatures $T^H$ reported below have been determined by calculation.

Comparative Test 1

During the first 8000 operating hours, 110 l (STP)/h of the reaction gas mixture were conducted through the reaction tube. The temperature $T^{SB}$ was adjusted such that the propylene conversion C (based on a single pass of the reaction gas mixture through the reaction tube) was always 95 mol %. The pressure at the inlet into the reaction tube was 1.2 bar absolute.

Table I below shows, as a function of operating time t(h) and unsupported catalyst used: $T^H$ (in ° C.); $T^{SB}$ (in ° C.); the total selectivity $S^{AC+AA}$ (in mol %) of target product formation (acrolein+acrylic acid).

TABLE I

| | t | | | | | | | |
|---|---|---|---|---|---|---|---|---|
| | 10 | 90 | 210 | 315 | 426 | 520 | 1000 | 8000 |
| Unsupported catalyst I | | | | | | | | |
| $T_I^H$ | 363 | 360 | 360 | 361 | 361 | 361 | 362 | 361 |
| $S_I^{AC+AA}$ | 92.4 | 93.7 | 93.8 | 93.9 | 94.0 | 94.1 | 94.2 | 94.1 |
| $T_I^{SB}$ | 318 | 315 | 315 | 316 | 315 | 315 | 316 | 315 |

TABLE I-continued

| | t | | | | | | | |
|---|---|---|---|---|---|---|---|---|
| | 10 | 90 | 210 | 315 | 426 | 520 | 1000 | 8000 |
| Unsupported catalyst II | | | | | | | | |
| $T_{II}^H$ | 364 | 364 | 364 | 363 | 363 | 364 | 364 | 364 |
| $S_{II}^{AC+AA}$ | 95.1 | 95.1 | 95.2 | 95.2 | 95.3 | 95.3 | 95.4 | 95.3 |
| $T_{II}^{SB}$ | 319 | 319 | 319 | 318 | 319 | 319 | 318 | 319 |

Comparative Test 2

The procedure was as in comparative test 1, except that, after the first 210 operating hours, the salt bath temperature, while simultaneously increasing the propylene conversion, was increased for an operating period of 226 operating hours to such an extent that $T^H$ during the 226 operating hours was approx. 430° C. After the aforementioned 226 operating hours, $T^{SB}$ was lowered again and adjusted until the end of the first 8000 operating hours in total such that C was always 95 mol %.

Table II below shows, as a function of operating time t(h) and unsupported catalyst used: $T^H$ (in ° C.); $T^{SB}$ (in ° C.); the total selectivity SAC+AA (in mol %).

TABLE II

| | t | | | | | | | |
|---|---|---|---|---|---|---|---|---|
| | 10 | 90 | 210 | 315 | 426 | 520 | 1000 | 8000 |
| Unsupported catalyst I | | | | | | | | |
| $T_I^H$ | 363 | 360 | 360 | 433 | 430 | 366 | 366 | 366 |
| $S_I^{AC+AA}$ | 92.4 | 93.7 | 93.8 | 85.7 | 86.0 | 95.9 | 96.0 | 95.9 |
| $T_I^{SB}$ | 318 | 315 | 315 | 380 | 380 | 321 | 322 | 322 |
| Unsupported catalyst II | | | | | | | | |
| $T_{II}^H$ | 364 | 364 | 364 | 430 | 428 | 370 | 369 | 370 |
| $S_{II}^{AC+AA}$ | 95.1 | 95.1 | 95.2 | 88.0 | 88.4 | 96.2 | 96.2 | 96.3 |
| $T_{II}^{SB}$ | 319 | 319 | 319 | 384 | 385 | 324 | 325 | 325 |

Inventive Test

The procedure was as in comparative test 1, except that, after the first 210 operating hours, the flow rate of reaction gas input mixture supplied to the reaction tube was increased for an operating period of 226 operating hours to 200 l (STP)/h (the pressure at the inlet into the reaction tube rose to 1.6 bar absolute). Simultaneously, the salt bath temperature $T^{SB}$ was adjusted such that, during the aforementioned 226 operating hours, the propylene conversion C of 95 mol % was maintained. As a result, $T^H$ assumed a value of approx. 430° C. during the 226 operating hours. After the 226 operating hours had ended, the flow rate of reaction gas input mixture supplied to the reaction tube was lowered again to 110 l (STP)/h. This value was maintained until the end of the first 8000 operating hours in total and $T^{SB}$ was adjusted again such that C was always 95 mol %.

Table III below shows, as a function of operating time t(h) and unsupported catalyst used: $T^H$ (in ° C.); $T^{SB}$ (in ° C.); the total selectivity $S^{AC+AA}$ (in mol %).

TABLE III

| | t | | | | | | | |
|---|---|---|---|---|---|---|---|---|
| | 10 | 90 | 210 | 315 | 426 | 520 | 1000 | 8000 |
| Unsupported catalyst I | | | | | | | | |
| $T_I^H$ | 363 | 360 | 360 | 431 | 429 | 364 | 365 | 365 |
| $S_I^{AC+AA}$ | 92.4 | 93.7 | 93.8 | 94.4 | 95.6 | 97.1 | 97.1 | 97.0 |
| $T_I^{SB}$ | 318 | 315 | 315 | 380 | 380 | 320 | 321 | 321 |
| Unsupported catalyst II | | | | | | | | |
| $T_{II}^H$ | 364 | 364 | 364 | 429 | 427 | 366 | 365 | 367 |
| $S_{II}^{AC+AA}$ | 95.1 | 95.1 | 95.2 | 94.5 | 95.4 | 96.5 | 96.4 | 96.5 |
| $T_{II}^{SB}$ | 319 | 319 | 319 | 380 | 380 | 322 | 323 | 323 |

The overall view of the three tests shows that the selectivity $S^{AC+AA}$ of target product formation viewed over the first 8000 operating hours in the inventive procedure has the best evolution over the operating time overall.

U.S. Provisional Patent Application No. 61/265137, filed Nov. 30, 2009, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

The invention claimed is:

1. A process for preparing (meth)acrolein by heterogeneously catalyzed gas phase partial oxidation, in which a reaction gas mixture is passed at elevated temperature through a fresh fixed catalyst bed present in a reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst bed is at least one multielement oxide which comprises the elements Mo, Fe and Bi and additionally at least one of the two elements Ni and Co, wherein the process, over the first 8000 operating hours of the fresh fixed catalyst bed, during which the reaction gas mixture supplied to the fixed catalyst bed at a loading of the fixed catalyst bed with the organic precursor compound of at least 40 l (STP)/l·h comprises at least 3% by volume of the organic precursor compound to be partially oxidized and, based on a single pass of the reaction gas mixture through the fixed catalyst bed, at least 90 mol % of the organic precursor compound present therein is converted and the highest temperature $T^H$ of the reaction gas mixture in the course of passage through the fixed catalyst bed is at least 300° C., is performed such that, during X=10 to 500 operating hours, the highest temperature $T^H$ of the reaction gas mixture as it passes through the fixed catalyst bed is 400 to 450° C. and, during the remaining 8000−X operating hours, is less than 400° C., and the loading of the fixed catalyst bed with the at least one organic precursor compound to be partially oxidized, averaged arithmetically over the time, for the X operating hours is greater than for the 8000−X operating hours.

2. The process according to claim 1, wherein X=20 to 450 operating hours.

3. The process according to claim 1, wherein X=30 to 400 operating hours.

4. The process according to claim 1, wherein $T^H$ during the X operating hours is 405 to 445° C.

5. The process according to claim 1, wherein $T^H$ during the X operating hours is 405 to 440° C.

6. The process according to claim 1, wherein $T^H$ during the 8000−X operating hours is 300 to 399° C.

7. The process according to claim 1, wherein $T^H$ during the 8000−X operating hours is 300 to 398° C.

8. The process according to claim 1, wherein $T^H$ during the 8000−X operating hours is 330 to 380° C.

9. The process according to claim 1, wherein, during at least 20% of the X operating hours, the loading at the particular time of the fixed catalyst bed with the at least one organic precursor compound to be partially oxidized is greater than the loading of the fixed catalyst bed with the at least one organic precursor compound to be partially oxidized, averaged arithmetically over the duration of the 8000−X operating hours.

10. A process for preparing (meth)acrolein by heterogeneously catalyzed gas phase partial oxidation of at least one organic precursor compound to be partially oxidized, in which a reaction gas mixture is passed at elevated temperature through the fresh fixed catalyst beds present in the reaction tubes of a tube bundle reactor and comprises, as well as at least one organic precursor compound to be partially oxidized and molecular oxygen as an oxidizing agent in a molar $O_2$:organic precursor compound ratio of $\geq 1$, at least one diluent gas which is essentially inert under the conditions of the heterogeneously catalyzed gas phase partial oxidation, and in which the active material of the catalysts of the fixed catalyst beds is at least one multielement oxide which comprises the elements Mo, Fe and Bi and additionally at least one of the two elements Ni and Co, wherein, in the first 8000 operating hours of the fresh fixed catalyst beds, the process in at least 50% of the reaction tubes present in the tube bundle reactor is a process according to claim 1.

* * * * *